US011560351B2

(12) United States Patent
Trabelsi et al.

(10) Patent No.: US 11,560,351 B2
(45) Date of Patent: Jan. 24, 2023

(54) METHODS AND COMPOSITIONS INCORPORATING ALKYL POLYGLYCOSIDE SURFACTANT FOR USE IN OIL AND/OR GAS WELLS

(71) Applicant: Flotek Chemistry, LLC, Houston, TX (US)

(72) Inventors: Siwar Trabelsi, Houston, TX (US); Randal M. Hill, Honor, MI (US)

(73) Assignee: Flotek Chemistry, LLC, Houston, TX (US)

( * ) Notice: Subject to any disclaimer, the term of this patent is extended or adjusted under 35 U.S.C. 154(b) by 0 days.

(21) Appl. No.: 17/194,952

(22) Filed: Mar. 8, 2021

(65) Prior Publication Data

US 2021/0198177 A1    Jul. 1, 2021

Related U.S. Application Data

(63) Continuation of application No. 16/454,511, filed on Jun. 27, 2019, now Pat. No. 10,941,106, which is a continuation of application No. 15/457,792, filed on Mar. 13, 2017, now Pat. No. 10,421,707, which is a continuation-in-part of application No. 14/212,763, filed on Mar. 14, 2014, now Pat. No. 9,884,988, which is a continuation-in-part of application No. 13/918,155, filed on Jun. 14, 2013, now Pat. No. 9,321,955, and a continuation-in-part of application No. 13/918,166, filed on Jun. 14, 2013, now abandoned, and a continuation-in-part of application No. 13/829,495, filed on Mar. 14, 2013, now Pat. No. 9,428,683, and a continuation-in-part of application No. 13/829,434, filed on Mar. 14, 2013, now Pat. No. 9,068,108.

(60) Provisional application No. 61/946,176, filed on Feb. 28, 2014.

(51) Int. Cl.
| | | |
|---|---|---|
| C09K 8/28 | (2006.01) | |
| C07C 69/007 | (2006.01) | |
| C09K 8/584 | (2006.01) | |
| C04B 28/02 | (2006.01) | |
| C09K 8/88 | (2006.01) | |
| C09K 8/68 | (2006.01) | |
| C07G 3/00 | (2006.01) | |
| C09K 8/467 | (2006.01) | |
| C09K 8/42 | (2006.01) | |
| C09K 8/40 | (2006.01) | |
| C09K 8/60 | (2006.01) | |
| C07C 31/20 | (2006.01) | |

(52) U.S. Cl.
CPC ............ *C07C 69/007* (2013.01); *C04B 28/02* (2013.01); *C07G 3/00* (2013.01); *C09K 8/28* (2013.01); *C09K 8/40* (2013.01); *C09K 8/42* (2013.01); *C09K 8/467* (2013.01); *C09K 8/584* (2013.01); *C09K 8/602* (2013.01); *C09K 8/68* (2013.01); *C09K 8/88* (2013.01); *C07C 31/205* (2013.01); *C07G 99/00* (2022.08)

(58) Field of Classification Search
CPC ..... C07C 69/007; C07C 31/205; C04B 28/02; C09K 8/28; C09K 8/40; C09K 8/42; C09K 8/467; C09K 8/584; C09K 8/602; C09K 8/68; C07G 17/00
See application file for complete search history.

(56) References Cited

U.S. PATENT DOCUMENTS

| | | | |
|---|---|---|---|
| 3,060,210 A | 4/1961 | De Groote et al. | |
| 3,047,062 A | 7/1962 | Meadors | |
| 3,347,789 A | 10/1967 | Dickson et al. | |
| 3,368,624 A | 2/1968 | Heuer et al. | |
| 3,483,923 A | 12/1969 | Darley | |
| 3,710,865 A | 1/1973 | Kiel | |
| 3,756,319 A | 9/1973 | Holm et al. | |
| 3,760,881 A | 9/1973 | Kiel | |
| 3,850,248 A | 11/1974 | Carney | |
| 3,919,411 A | 11/1975 | Glass et al. | |
| 4,005,020 A | 1/1977 | McCormick | |
| 4,101,425 A * | 7/1978 | Young | C09K 8/74 507/260 |
| 4,206,809 A | 6/1980 | Jones | |
| 4,233,165 A | 11/1980 | Salathiel et al. | |
| 4,276,935 A | 7/1981 | Hessert et al. | |
| 4,360,061 A | 11/1982 | Canter et al. | |
| 4,414,128 A | 11/1983 | Goffinet | |
| 4,472,291 A | 9/1984 | Rosano | |
| 4,511,488 A * | 4/1985 | Matta | C11D 3/43 510/362 |

(Continued)

FOREIGN PATENT DOCUMENTS

| | | |
|---|---|---|
| CN | 102127414 | 7/2011 |
| CN | 102277143 | 12/2011 |

(Continued)

OTHER PUBLICATIONS

U.S. Appl. No. 16/430,138, filed Jun. 3, 2019, Champagne et al.
U.S. Appl. No. 16/916,199, filed Jun. 30, 2020, Hill et al.
PCT/US2014/029079, Jul. 31, 2014, International Search Report and Written Opinion.
PCT/US2018/021983, May 23, 2018, International Search Report and Written Opinion.
International Search Report and Written Opinion dated Jul. 31, 2014 for Application No. PCT/US2014/029079.

(Continued)

*Primary Examiner* — Silvana C Runyan
(74) *Attorney, Agent, or Firm* — Wolf, Greenfield & Sacks, P.C.

(57) ABSTRACT

Methods and compositions comprising an emulsion or a microemulsion for use treating an oil and/or gas well are provided. In some embodiments, the emulsion or the microemulsion comprises an aqueous phase, a solvent, a surfactant comprising alkyl polyglycoside, an alcohol, and, optionally, one or more additives.

15 Claims, No Drawings

(56) References Cited

U.S. PATENT DOCUMENTS

| | | | |
|---|---|---|---|
| 4,614,236 A * | 9/1986 | Watkins | C09K 8/26 |
| | | | 134/36 |
| 4,650,000 A | 3/1987 | Andreasson et al. | |
| 4,844,756 A | 7/1989 | Forsberg | |
| 5,008,026 A | 4/1991 | Gardner et al. | |
| 5,034,140 A | 7/1991 | Gardner et al. | |
| 5,076,954 A * | 12/1991 | Loth | C11D 17/0021 |
| | | | 134/40 |
| 5,083,613 A | 1/1992 | Gregoli et al. | |
| 5,095,989 A | 3/1992 | Prukop | |
| 5,217,531 A | 6/1993 | Cheung | |
| 5,247,995 A | 9/1993 | Tjon-Joe-Pin et al. | |
| 5,310,002 A | 5/1994 | Blauch et al. | |
| 5,356,482 A | 10/1994 | Mehta et al. | |
| 5,567,675 A | 10/1996 | Romocki | |
| 5,587,354 A | 12/1996 | Duncan, Jr. | |
| 5,587,357 A | 12/1996 | Rhinesmith | |
| 5,604,195 A | 2/1997 | Misselyn et al. | |
| 5,652,200 A | 7/1997 | Davies et al. | |
| 5,665,689 A | 9/1997 | Durbut | |
| 5,676,763 A | 10/1997 | Salisbury et al. | |
| 5,697,458 A | 12/1997 | Carney | |
| 5,707,940 A | 1/1998 | Bush et al. | |
| 5,762,138 A | 6/1998 | Ford et al. | |
| 5,784,386 A | 7/1998 | Norris | |
| 5,811,383 A | 9/1998 | Klier et al. | |
| 5,830,831 A | 11/1998 | Chan et al. | |
| 5,874,386 A | 2/1999 | Chan et al. | |
| 5,925,233 A | 7/1999 | Miller et al. | |
| 5,975,206 A | 11/1999 | Woo et al. | |
| 5,977,032 A | 11/1999 | Chan | |
| 5,990,072 A | 11/1999 | Gross et al. | |
| 5,996,692 A | 12/1999 | Chan et al. | |
| 6,046,140 A | 4/2000 | Woo et al. | |
| 6,090,754 A | 7/2000 | Chan et al. | |
| 6,110,885 A | 8/2000 | Chan | |
| 6,112,814 A | 9/2000 | Chan et al. | |
| 6,165,946 A | 12/2000 | Mueller et al. | |
| 6,173,776 B1 | 1/2001 | Furman et al. | |
| 6,191,090 B1 | 2/2001 | Mondin et al. | |
| 6,228,830 B1 | 5/2001 | Vlasblom | |
| 6,260,621 B1 | 7/2001 | Furman et al. | |
| 6,302,209 B1 | 10/2001 | Thompson, Sr. et al. | |
| 6,364,020 B1 | 4/2002 | Crawshaw et al. | |
| 6,486,115 B1 | 11/2002 | Weaver et al. | |
| 6,581,687 B2 | 6/2003 | Collins et al. | |
| 6,593,279 B2 | 7/2003 | Von Krosigk et al. | |
| 6,613,720 B1 | 9/2003 | Feraud et al. | |
| 6,729,402 B2 | 5/2004 | Chang et al. | |
| 6,770,603 B1 | 8/2004 | Sawdon et al. | |
| 6,793,025 B2 | 9/2004 | Patel et al. | |
| 6,800,593 B2 | 10/2004 | Dobson, Jr. et al. | |
| 6,818,595 B2 | 11/2004 | Benton et al. | |
| 6,911,417 B2 | 6/2005 | Chan et al. | |
| 6,914,040 B2 | 7/2005 | Deak et al. | |
| 6,939,832 B2 | 9/2005 | Collins | |
| 6,984,610 B2 | 1/2006 | VonKrosigk et al. | |
| 7,021,378 B2 | 4/2006 | Prukop | |
| 7,134,496 B2 | 11/2006 | Jones et al. | |
| 7,205,262 B2 | 4/2007 | Schwartz et al. | |
| 7,205,264 B2 | 4/2007 | Boles | |
| 7,231,976 B2 | 6/2007 | Berry et al. | |
| 7,380,606 B2 | 6/2008 | Pursley et al. | |
| 7,392,844 B2 | 7/2008 | Berry et al. | |
| 7,407,915 B2 | 8/2008 | Jones et al. | |
| 7,468,402 B2 | 12/2008 | Yang et al. | |
| 7,481,273 B2 | 1/2009 | Javora et al. | |
| 7,514,390 B2 | 4/2009 | Chan | |
| 7,514,391 B2 | 4/2009 | Chan | |
| 7,533,723 B2 | 5/2009 | Hughes et al. | |
| 7,543,644 B2 | 6/2009 | Huang et al. | |
| 7,543,646 B2 | 6/2009 | Huang et al. | |
| 7,544,639 B2 | 6/2009 | Pursley et al. | |
| 7,547,665 B2 | 6/2009 | Welton et al. | |
| 7,552,771 B2 | 6/2009 | Eoff et al. | |
| 7,559,369 B2 | 7/2009 | Roddy et al. | |
| 7,581,594 B2 | 9/2009 | Tang | |
| 7,615,516 B2 | 11/2009 | Yang et al. | |
| 7,621,334 B2 | 11/2009 | Welton et al. | |
| 7,622,436 B2 | 11/2009 | Tuzi et al. | |
| 7,655,603 B2 | 2/2010 | Crews | |
| 7,677,311 B2 | 3/2010 | Abad et al. | |
| 7,687,439 B2 | 3/2010 | Jones et al. | |
| 7,709,421 B2 | 5/2010 | Jones et al. | |
| 7,712,534 B2 | 5/2010 | Bryant et al. | |
| 7,727,936 B2 | 6/2010 | Pauls et al. | |
| 7,727,937 B2 | 6/2010 | Pauls et al. | |
| 7,730,958 B2 | 6/2010 | Smith | |
| 7,825,073 B2 | 11/2010 | Welton et al. | |
| 7,833,943 B2 | 11/2010 | Van Zanten et al. | |
| 7,838,467 B2 | 11/2010 | Jones et al. | |
| 7,846,877 B1 | 12/2010 | Robb | |
| 7,851,414 B2 | 12/2010 | Yang et al. | |
| 7,855,168 B2 | 12/2010 | Fuller et al. | |
| 7,857,051 B2 | 12/2010 | Abad et al. | |
| 7,886,824 B2 | 2/2011 | Kakadjian et al. | |
| 7,893,010 B2 | 2/2011 | Ali et al. | |
| 7,902,123 B2 | 3/2011 | Harrison et al. | |
| 7,906,464 B2 | 3/2011 | Davidson | |
| 7,910,524 B2 | 3/2011 | Welton et al. | |
| 7,931,088 B2 | 4/2011 | Stegemoeller et al. | |
| 7,960,314 B2 | 6/2011 | Van Zanten et al. | |
| 7,960,315 B2 | 6/2011 | Welton et al. | |
| 7,963,720 B2 | 6/2011 | Hoag et al. | |
| 7,971,659 B2 | 7/2011 | Gatlin et al. | |
| 7,976,241 B2 | 7/2011 | Hoag et al. | |
| 7,989,404 B2 | 8/2011 | Kakadjian et al. | |
| 7,992,656 B2 | 8/2011 | Dusterhoft et al. | |
| 7,998,911 B1 | 8/2011 | Berger et al. | |
| 8,043,996 B2 | 10/2011 | Harris | |
| 8,053,396 B2 | 11/2011 | Huff et al. | |
| 8,053,397 B2 | 11/2011 | Huang et al. | |
| 8,057,682 B2 | 11/2011 | Hoag et al. | |
| 8,091,644 B2 | 1/2012 | Clark et al. | |
| 8,091,645 B2 | 1/2012 | Quintero et al. | |
| 8,091,646 B2 | 1/2012 | Quintero et al. | |
| 8,100,190 B2 | 1/2012 | Weaver et al. | |
| 8,148,303 B2 | 4/2012 | Van Zanten et al. | |
| 8,183,182 B2 | 5/2012 | Oliveira et al. | |
| 8,206,062 B2 | 6/2012 | Hoag et al. | |
| 8,207,096 B2 | 6/2012 | van Zanten et al. | |
| 8,210,263 B2 | 7/2012 | Quintero et al. | |
| 8,220,546 B2 | 7/2012 | Kakadjian et al. | |
| 8,227,382 B2 | 7/2012 | Dakin et al. | |
| 8,231,947 B2 | 7/2012 | Vaidya et al. | |
| 8,235,120 B2 | 8/2012 | Quintero et al. | |
| 8,242,059 B2 | 8/2012 | Sawdon | |
| 8,293,687 B2 | 10/2012 | Giffin | |
| 8,342,241 B2 | 1/2013 | Hartshorne et al. | |
| 8,349,771 B2 | 1/2013 | Seth et al. | |
| 8,356,667 B2 | 1/2013 | Quintero et al. | |
| 8,357,639 B2 | 1/2013 | Quintero et al. | |
| 8,372,789 B2 | 2/2013 | Harris et al. | |
| 8,383,560 B2 | 2/2013 | Pich et al. | |
| 8,403,051 B2 | 3/2013 | Huang et al. | |
| 8,404,623 B2 | 3/2013 | Robb et al. | |
| 8,413,721 B2 | 4/2013 | Welton et al. | |
| 8,415,279 B2 | 4/2013 | Quintero et al. | |
| 8,431,620 B2 | 4/2013 | Del Gaudio et al. | |
| 8,453,741 B2 | 6/2013 | van Zanten | |
| 8,492,445 B2 | 7/2013 | Renault et al. | |
| 8,499,832 B2 | 8/2013 | Crews et al. | |
| 8,517,100 B2 | 8/2013 | Ali et al. | |
| 8,517,104 B2 | 8/2013 | Kieffer | |
| 8,524,643 B2 | 9/2013 | Huff et al. | |
| 8,551,926 B2 | 10/2013 | Huang et al. | |
| 8,592,350 B2 | 11/2013 | van Zanten et al. | |
| 8,684,079 B2 | 4/2014 | Wattenbarger et al. | |
| 8,778,850 B2 | 7/2014 | Andrecola | |
| 8,865,632 B1 | 10/2014 | Parnell et al. | |
| 9,238,786 B2 | 1/2016 | Ojima et al. | |
| 9,850,418 B2 | 12/2017 | Champagne et al. | |
| 9,868,893 B2 | 1/2018 | Saboowala et al. | |
| 9,884,988 B2 | 2/2018 | Dismuke et al. | |

(56) References Cited

U.S. PATENT DOCUMENTS

| | | |
|---|---|---|
| 10,000,693 B2 | 6/2018 | Hill et al. |
| 10,005,948 B2 | 6/2018 | Champagne et al. |
| 10,081,760 B2 | 9/2018 | Ngantung et al. |
| 10,144,862 B2 | 12/2018 | Zelenev et al. |
| 10,196,557 B2 | 2/2019 | Hill et al. |
| 10,280,360 B2 | 5/2019 | Champagne et al. |
| 10,287,483 B2 | 5/2019 | Saboowala et al. |
| 10,294,757 B2 | 5/2019 | Fursdon-Welsh et al. |
| 10,294,764 B2 | 5/2019 | Champagne et al. |
| 10,308,859 B2 | 6/2019 | Champagne et al. |
| 10,421,707 B2 | 9/2019 | Trabelsi et al. |
| 10,544,355 B2 | 1/2020 | Hill et al. |
| 10,577,531 B2 | 3/2020 | Pursley et al. |
| 10,590,332 B2 | 3/2020 | Penny et al. |
| 10,696,887 B2 | 6/2020 | Dismuke et al. |
| 10,703,960 B2 | 7/2020 | Hill et al. |
| 10,717,919 B2 | 7/2020 | Germack et al. |
| 10,731,071 B2 | 8/2020 | Saboowala et al. |
| 10,738,235 B2 | 8/2020 | Hill et al. |
| 10,934,472 B2 | 3/2021 | Smith, Jr. |
| 10,941,106 B2 | 3/2021 | Trabelsi et al. |
| 2001/0007663 A1 | 7/2001 | Von Corswant |
| 2003/0022944 A1 | 1/2003 | Gumkowski et al. |
| 2003/0069143 A1 | 4/2003 | Collins |
| 2003/0162689 A1 | 8/2003 | Schymitzek et al. |
| 2003/0166472 A1 | 9/2003 | Pursley et al. |
| 2003/0232095 A1 | 12/2003 | Garti et al. |
| 2005/0209107 A1 | 9/2005 | Pursley et al. |
| 2006/0014648 A1 | 1/2006 | Milson et al. |
| 2006/0096757 A1 | 5/2006 | Berry et al. |
| 2006/0204468 A1 | 9/2006 | Allef et al. |
| 2006/0211593 A1 | 9/2006 | Smith et al. |
| 2006/0258541 A1 | 11/2006 | Crews |
| 2007/0123445 A1 | 5/2007 | Tuzi et al. |
| 2007/0128232 A1 | 6/2007 | Rahse |
| 2007/0135310 A1 | 6/2007 | Qu et al. |
| 2007/0293404 A1 | 12/2007 | Hutchins et al. |
| 2007/0295368 A1 | 12/2007 | Harrison et al. |
| 2008/0274918 A1 | 11/2008 | Quintero et al. |
| 2008/0287324 A1 | 11/2008 | Pursley et al. |
| 2009/0078415 A1 | 3/2009 | Fan et al. |
| 2009/0137432 A1 | 5/2009 | Sullivan et al. |
| 2009/0159288 A1 | 6/2009 | Horvath Szabo et al. |
| 2009/0221456 A1 | 9/2009 | Harrison et al. |
| 2009/0260819 A1 | 10/2009 | Kurian et al. |
| 2009/0275488 A1 | 11/2009 | Zamora et al. |
| 2009/0281004 A1 | 11/2009 | Ali et al. |
| 2010/0006286 A1 | 1/2010 | Oliveira et al. |
| 2010/0022421 A1 | 1/2010 | Gutierrez et al. |
| 2010/0152069 A1* | 6/2010 | Harris ..................... C09K 8/72 507/201 |
| 2010/0173805 A1 | 7/2010 | Pomerleau |
| 2010/0216670 A1 | 8/2010 | Del Gaudio et al. |
| 2010/0243248 A1 | 9/2010 | Golomb et al. |
| 2010/0252267 A1 | 10/2010 | Harris et al. |
| 2010/0263863 A1 | 10/2010 | Quintero et al. |
| 2010/0272765 A1 | 10/2010 | Ho et al. |
| 2010/0307757 A1 | 12/2010 | Blow et al. |
| 2010/0314118 A1 | 12/2010 | Quintero et al. |
| 2011/0021386 A1 | 1/2011 | Ali et al. |
| 2011/0105369 A1 | 5/2011 | Reddy |
| 2011/0136706 A1 | 6/2011 | Carroll et al. |
| 2011/0146983 A1 | 6/2011 | Sawdon |
| 2011/0190174 A1 | 8/2011 | Weerasooriya et al. |
| 2011/0220353 A1 | 9/2011 | Bittner et al. |
| 2011/0237467 A1 | 9/2011 | Cornette et al. |
| 2011/0253365 A1 | 10/2011 | Crews et al. |
| 2011/0290491 A1 | 12/2011 | Gupta et al. |
| 2012/0004146 A1 | 1/2012 | Van Zanten et al. |
| 2012/0015852 A1 | 1/2012 | Quintero et al. |
| 2012/0035085 A1 | 2/2012 | Parnell et al. |
| 2012/0071366 A1 | 3/2012 | Falana et al. |
| 2012/0080232 A1 | 4/2012 | Muller et al. |
| 2012/0129738 A1 | 5/2012 | Gupta et al. |
| 2012/0149626 A1 | 6/2012 | Fluck et al. |
| 2012/0168165 A1 | 7/2012 | Holcomb et al. |
| 2012/0181019 A1 | 7/2012 | Saini et al. |
| 2012/0193095 A1 | 8/2012 | Varadaraj et al. |
| 2012/0208726 A1 | 8/2012 | Smith et al. |
| 2012/0234548 A1 | 9/2012 | Dyer |
| 2012/0241155 A1 | 9/2012 | Ali et al. |
| 2012/0241220 A1 | 9/2012 | Quintero et al. |
| 2012/0255887 A1 | 10/2012 | Holms et al. |
| 2012/0261120 A1 | 10/2012 | Del Gaudio et al. |
| 2012/0285690 A1 | 11/2012 | Weaver et al. |
| 2012/0285694 A1 | 11/2012 | Morvan et al. |
| 2012/0318504 A1 | 12/2012 | Fan et al. |
| 2012/0318515 A1 | 12/2012 | Cawiezel et al. |
| 2012/0322697 A1 | 12/2012 | Zhang |
| 2012/0325492 A1 | 12/2012 | Fefer et al. |
| 2013/0029883 A1 | 1/2013 | Dismuke et al. |
| 2013/0048281 A1 | 2/2013 | Van Zanten et al. |
| 2013/0079255 A1 | 3/2013 | Del Gaudio et al. |
| 2013/0109597 A1 | 5/2013 | Sarkar et al. |
| 2013/0133886 A1 | 5/2013 | Quintero |
| 2013/0137611 A1 | 5/2013 | Pierce et al. |
| 2013/0146288 A1 | 6/2013 | Smith et al. |
| 2013/0146545 A1 | 6/2013 | Pabalan et al. |
| 2013/0153232 A1 | 6/2013 | Bobier et al. |
| 2013/0153234 A1 | 6/2013 | Bobier et al. |
| 2013/0192826 A1 | 8/2013 | Kurian et al. |
| 2013/0233559 A1 | 9/2013 | van Zanten et al. |
| 2013/0244913 A1 | 9/2013 | Maberry et al. |
| 2013/0261033 A1 | 10/2013 | Nguyen |
| 2013/0292121 A1 | 11/2013 | Penny et al. |
| 2014/0005079 A1 | 1/2014 | Dahanayake et al. |
| 2014/0110344 A1 | 4/2014 | Hoag et al. |
| 2014/0202700 A1 | 7/2014 | Blair |
| 2014/0262261 A1 | 9/2014 | Hill et al. |
| 2014/0262274 A1 | 9/2014 | Dismuke et al. |
| 2014/0262288 A1 | 9/2014 | Penny et al. |
| 2014/0274817 A1 | 9/2014 | Hill et al. |
| 2014/0274822 A1 | 9/2014 | Dismuke et al. |
| 2014/0284053 A1 | 9/2014 | Germack et al. |
| 2014/0284057 A1 | 9/2014 | Champagne et al. |
| 2014/0299325 A1 | 10/2014 | Zelenev et al. |
| 2014/0332212 A1 | 11/2014 | Ayers et al. |
| 2014/0367107 A1 | 12/2014 | Hill et al. |
| 2014/0371115 A1 | 12/2014 | Hill et al. |
| 2015/0053404 A1 | 2/2015 | Penny et al. |
| 2015/0068755 A1 | 3/2015 | Hill et al. |
| 2015/0184061 A1 | 7/2015 | Saboowala et al. |
| 2015/0197683 A1 | 7/2015 | Hategan et al. |
| 2016/0096989 A1 | 4/2016 | Ngantung et al. |
| 2017/0096594 A1 | 4/2017 | Champagne et al. |
| 2017/0275518 A1 | 9/2017 | Trabelsi et al. |
| 2017/0335179 A1 | 11/2017 | Ngantung et al. |
| 2018/0134941 A1 | 5/2018 | Saboowala et al. |
| 2018/0171213 A1 | 6/2018 | Hill et al. |
| 2019/0031948 A1 | 1/2019 | Hill et al. |
| 2019/0055457 A1 | 2/2019 | Smith, Jr. et al. |
| 2019/0055458 A1 | 2/2019 | Smith, Jr. et al. |
| 2019/0055459 A1 | 2/2019 | Zelenev et al. |
| 2019/0085236 A1 | 3/2019 | Saboowala et al. |
| 2019/0090476 A1 | 3/2019 | Smith, Jr. et al. |
| 2019/0100689 A1 | 4/2019 | Zelenev et al. |
| 2019/0169488 A1 | 6/2019 | Hill et al. |
| 2019/0169492 A1 | 6/2019 | Hill et al. |
| 2019/0241796 A1 | 8/2019 | Mast et al. |
| 2019/0264094 A1 | 8/2019 | Hill et al. |
| 2019/0284467 A1 | 9/2019 | Forbes et al. |
| 2019/0315674 A1 | 10/2019 | Trabelsi et al. |
| 2019/0316021 A1 | 10/2019 | Champagne et al. |
| 2020/0157412 A1 | 5/2020 | Hill et al. |
| 2020/0216749 A1 | 7/2020 | Penny et al. |
| 2020/0332177 A1 | 10/2020 | Hill et al. |
| 2020/0369950 A1 | 11/2020 | Hill et al. |
| 2021/0108132 A1 | 4/2021 | Trabelsi |

FOREIGN PATENT DOCUMENTS

| | | |
|---|---|---|
| CN | 103614128 | 3/2014 |
| CN | 103642477 | 3/2014 |
| EP | 1 051 237 B1 | 11/2003 |

(56) References Cited

FOREIGN PATENT DOCUMENTS

| | | |
|---|---|---|
| EP | 1 378 554 A1 | 1/2004 |
| EP | 1 786 879 B1 | 2/2012 |
| EP | 2 195 400 B1 | 8/2012 |
| EP | 1 880 081 B1 | 3/2013 |
| WO | WO 99/049182 | 9/1999 |
| WO | WO 03/000834 A1 | 1/2003 |
| WO | WO 2005/048706 | 6/2005 |
| WO | WO 2007/011475 | 1/2007 |
| WO | WO 2012/158645 | 11/2012 |
| WO | WO 2017/099709 A1 | 6/2017 |
| WO | WO 2018/111229 A1 | 6/2018 |

OTHER PUBLICATIONS

International Search Report and Written Opinion for PCT/US2018/021983 dated May 23, 2018.

[No Author Listed], The HLB system: a time-saving guide to emulsifier selection. ICI Americas Inc. 1976. 22 pages.

ADM, Evolution Chemicals E5789-117 Description. Jun. 2014. 1 page.

Brost et al., Surfactants assist water-in-oil monitoring by fluroescence. World Oil. Oct. 2008;229(10):12 pages.

Champagne et al., Critical assessment of microemulsion technology for enhancing fluid recovery from tight gas formations and propped fractures. SPE European Formation Damage Conference. Noordwijk, The Netherlands. Jun. 7-10, 2011. SPE-144095. 10 pages.

Crafton et al., Micro-emulsion effectiveness for twenty four wells, Eastern Green River, Wyoming. 2009 SPE Rocky Mountain Petroleum Technology Conference. Denver, Colorado, USA, Apr. 14-16, 2009. SPE-123280. 13 pages.

HAW, The HLB system: a time saving guide to surfactant selection. Presentation to the Midwest chapter of the society of cosmetic chemists. Uniqema. Mar. 9, 2004. 39 slides.

Howard et al., Comparison of flowback aids: understanding their capillary pressure and wetting properties. SPE Production & Operations. Aug. 2010:376-87.

Kunieda et al. Evaluation of hydrophile-lipophile balance (HLB) of nonionic surfactants. J Colloid and Interface Sci. Sep. 1985;107(1):107-21.

Yang et al., Optimizing nanoemulsions as fluid flowback additives in enhancing tight gas production. J Petroleum Sci Eng. 2014;121:122-5.

Zelenev et al., Microemulsion technology for improved fluid recovery and enhanced core permeability to gas. 2009 SPE European Formation Damage Conference. Scheveningen, The Netherlands. May 27-29, 2009. SPE 122109. 13 pages.

Zelenev et al., Microemulsion-assisted fluid recovery and improved permeability to gas in shale formations. 2010 SPE International Symposium and Exhibition on Formation Damage Control. Lafayette, Louisiana, USA. Feb. 10-12, 2010. SPE 127922. 7 pages.

Zelenev, Surface energy of north American shales and its role in interaction of shale with surfactants and microemulsions. SPE International Symposium on Oilfield Chemistry. The Woodlands, Texas, USA. Apr. 11-13, 2011. SPE-141459. 7 pages.

* cited by examiner

METHODS AND COMPOSITIONS INCORPORATING ALKYL POLYGLYCOSIDE SURFACTANT FOR USE IN OIL AND/OR GAS WELLS

RELATED APPLICATIONS

This application is a continuation of U.S. patent application Ser. No. 16/454,511, filed Jun. 27, 2019, which is a continuation of U.S. patent application Ser. No. 15/457,792 (now U.S. Pat. No. 10,421,707), filed Mar. 13, 2017, which is a continuation-in-part of U.S. patent application Ser. No. 14/212,763 (now U.S. Pat. No. 9,884,988), filed Mar. 14, 2014, which claims priority to U.S. Provisional Application No. 61/946,176, filed Feb. 28, 2014, and is also a continuation-in-part of U.S. patent application Ser. No. 13/829,495 (now U.S. Pat. No. 9,428,683), filed Mar. 14, 2013, a continuation-in-part of U.S. patent application Ser. No. 13/829,434 (now U.S. Pat. No. 9,068,108), filed Mar. 14, 2013; a continuation-in-part of U.S. patent application Ser. No. 13/918,155 (now U.S. Pat. No. 9,321,955), filed Jun. 14, 2013; and a continuation-in-part of U.S. patent application Ser. No. 13/918,166 (now abandoned) filed Jun. 14, 2013, each of these U.S. patents and the U.S. published application are incorporated herein by reference in their entirety for all purposes.

FIELD OF INVENTION

Methods and compositions comprising an emulsion or a microemulsion for use in treating an oil and/or gas well are provided.

BACKGROUND OF INVENTION

Emulsions and/or microemulsions are commonly employed in a variety of operations related to the extraction of hydrocarbons, such as well stimulation. Subterranean formations are often stimulated to improve recovery of hydrocarbons. Common stimulation techniques include hydraulic fracturing. Hydraulic fracturing consists of the high pressure injection of a fluid containing suspended proppant into the wellbore in order to create fractures in the rock formation and facilitate production from low permeability zones. All chemicals pumped downhole in an oil and/or gas well can filter through the reservoir rock and block pore throats with the possibility of creating formation damage. It is well known that fluid invasion can significantly reduce hydrocarbon production from a well. In order to reduce fluid invasion, emulsions or microemulsions are generally added to the well-treatment fluids to help unload the residual aqueous treatment from the formation.

Accordingly, although a number of emulsions or microemulsions are known in the art, there is a continued need for more effective emulsions or microemulsions for use in treatment of an oil and/or gas well.

SUMMARY OF INVENTION

Methods and compositions comprising an emulsion or a microemulsion for use in treating an oil and/or gas well having a wellbore are provided.

In some embodiments, a method of treating an oil and/or gas well having a wellbore is provided comprising: injecting a fluid comprising an emulsion or a microemulsion into the wellbore, wherein the emulsion or the microemulsion comprises an aqueous phase; a surfactant comprising alkyl polyglycoside; a solvent selected from the group consisting of terpene, alkyl aliphatic carboxylic acid ester, and combinations thereof; and an alcohol selected from the group consisting of butanol, amyl alcohol, and combinations thereof.

In some embodiments, a composition for use in an oil and/or gas well having a wellbore is provided comprising a fluid and an emulsion or a microemulsion, wherein the emulsion or the microemulsion comprises an aqueous phase; a surfactant comprising alkyl polyglycoside; a solvent selected from the group consisting of terpene, alkyl aliphatic carboxylic acid ester, and combinations thereof; and an alcohol selected from the group consisting of butanol, amyl alcohol, and combinations thereof.

Other aspects, embodiments, and features of the methods and compositions will become apparent from the following detailed description. All patent applications and patents incorporated herein by reference are incorporated by reference in their entirety. In case of conflict, the present specification, including definitions, will control.

DETAILED DESCRIPTION

Methods and compositions comprising an emulsion or a microemulsion for use in treating an oil and/or gas well are provided. In some embodiments, a microemulsion may comprise an aqueous phase, a solvent (e.g., terpene and/or methyl aliphatic carboxylic acid ester), a surfactant comprising alkyl polyglycoside ("APG"), an alcohol (e.g., an alcohol functioning as a co-solvent, such as butanol or amyl alcohol), and optionally other additives (e.g., a freezing point depression agent, a demulsifier, etc.). In some embodiments, the methods and compositions relate to various aspects of the life cycle of an oil and/or gas well (e.g., fracturing fluids, drilling, mud displacement, casing, cementing, perforating, stimulation, remediation, kill fluids, enhanced oil recovery/improved oil recovery, etc.). In some embodiments, an emulsion or a microemulsion is added to a fluid utilized in the life cycle of a well thereby increasing hydrocarbon (e.g., liquid or gaseous) production of the well, improving recovery of the fluid and/or other fluids, and/or preventing or minimizing damage to the well caused by exposure to the fluid (e.g., from imbibition). In some embodiments, a method of treating an oil and/or gas well having a wellbore comprises injecting a fluid comprising an emulsion or a microemulsion into the wellbore.

Embodiments of the disclosed microemulsions overcome shortcomings of generally known microemulsions, which have been shown to be generally incompatible with a wide range of conditions. For example, many commonly used surfactants for microemulsions are useful only within a certain temperature range even though, in reality, oil field reservoirs vary widely in actual bottom hole or formation temperatures. Likewise, known compositions that form transparent microemulsions at surface temperatures may be well above their cloud point at bottom hole temperatures. Previous combinations of surfactants have been found to broaden the temperature range, but at the cost of compatibility with other components in the fluid system. Some common surfactants become insoluble in the high salinity brines often found in oil-bearing and gas-bearing formations.

Embodiments of the presently disclosed microemulsions may provide several advantages over previous microemulsions. For example, embodiments of the disclosed microemulsions are compatible with a wide range of water salinities (e.g., fresh, flowback and produced waters or mixtures thereof) and temperatures. This range of compatibility may prevent the microemulsion from undergoing phase separation during use which, in some circumstances, could decrease the microemulsion's efficacy.

According to some embodiments, the disclosed emulsions or microemulsions are able to lower capillary pressure and promote unloading at higher temperatures when used in applications where a wide range of temperatures and/or salinities may be encountered, such as multi-stage hydraulic fracturing in horizontal, lateral, or deviated wells, which may require millions of gallons of water per well. According to certain embodiments, the disclosed emulsions and microemulsions facilitate unloading of the aqueous treatment fluid from deep in the formation. According to certain embodiments, emulsions and microemulsions disclosed herein, provide for high performance in these and other difficult conditions, using renewable plant-based materials in a simple composition with a minimum number of components.

Additional details regarding the emulsions or microemulsions, as well as the applications of the emulsions or microemulsions, are described herein.

I. Emulsions and Microemulsions

It should be understood, that while much of the description herein focuses on microemulsions, this is by no means limiting, and emulsions may be employed where appropriate.

In some embodiments, an emulsion or a microemulsion comprises an aqueous phase, a solvent, a surfactant, and an alcohol (which may function as a co-solvent). In some embodiments, the emulsion or the microemulsion further comprises additional additives. Details of each of the components of the emulsions or the microemulsions are described in detail herein. In disclosed embodiments, the components of the emulsions or the microemulsions are selected so as to provide a desired performance over a wide range of temperatures and salinities.

In some embodiments, the emulsion or the microemulsion comprises an aqueous phase; a solvent comprising terpene (e.g., d-limonene) and/or alkyl aliphatic carboxylic acid ester (e.g., methyl aliphatic carboxylic acid ester, also referred to as methyl ester); a surfactant comprising alkyl polyglycoside; and an alcohol (e.g., butanol and/or amyl alcohol). The alcohol may function as a co-solvent.

In some embodiments the terpene comprises d-limonene. In some embodiments the alkyl aliphatic carboxylic acid ester comprises methyl ester. In some embodiments the alcohol comprises butanol and/or amyl alcohol.

In some embodiments, the emulsion or the microemulsion comprises an aqueous phase; a solvent comprising d-limonene and/or methyl ester; a surfactant comprising alkyl polyglycoside; and an alcohol comprising butanol and/or amyl alcohol.

In some embodiments additives may be added to the emulsion or microemulsion. For example, the emulsion or the microemulsion may comprise a freezing point depression agent (e.g., propylene glycol) and/or a demulsifier, without disturbing the stability of the emulsion or the microemulsion over a range of salinities or temperatures. Other potential additives are discussed below. In some embodiments, the emulsion or the microemulsion consists essentially of an aqueous phase; a solvent comprising d-limonene and/or methyl ester; a surfactant comprising alkyl polyglycoside; an alcohol comprising butanol and/or amyl alcohol; and, optionally, one or more additives.

In some embodiments, the aqueous phase is present in the emulsion or the microemulsion in an amount of between about 10 wt % and about 70 wt %, or between about 35 wt % and about 60 wt %. In some embodiments, the alkyl polyglycoside surfactant is present in the emulsion or the microemulsion in an amount of between about 10 wt % and about 25 wt % or between about 16 wt % and about 24 wt %. In some embodiments, the solvent is present in the emulsion or the microemulsion in an amount between about 1 wt % and about 20 wt % or between about 9 wt % and about 17 wt %. In some embodiments, the alcohol (e.g., alcohol co-solvent) is present in the emulsion or the microemulsion in an amount between about 2 wt % and about 15 wt % or between about 4 wt % and about 9 wt %.

In some embodiments, the emulsion or the microemulsion comprises an aqueous phase; a solvent comprising an oleaginous hydrocarbon solvent; a surfactant comprising an alkyl polyglycoside; and a co-surfactant comprising an oxygenated co-surfactant. In some embodiments, the emulsion or the microemulsion comprises between about 10 wt % and about 60 wt % aqueous phase (e.g., water). In some embodiments, the emulsion or the microemulsion consists essentially of an aqueous phase; a solvent comprising an oleaginous hydrocarbon solvent; a surfactant comprising an alkyl polyglycoside; a co-surfactant comprising an oxygenated co-surfactant; and, optionally, one or more additives. In some embodiments, the emulsion or the microemulsion comprises between about 10 wt % and about 60 wt % aqueous phase (e.g., water). In some embodiments, the emulsion or the microemulsion comprises between about 1 wt % and about 17 wt % solvent. In some embodiments, the emulsion or the microemulsion comprises between about 10 wt % and about 25 wt % surfactant. In some embodiments, the emulsion or the microemulsion comprises between about 2 wt % and about 15 wt % oxygenated co-surfactant. In some embodiments, the emulsion or microemulsion comprises between about 10 wt % and about 60 wt % aqueous phase (e.g., water), between about 1 wt % and about 17 wt % solvent, between about 10 wt % and about 25 wt % surfactant, and between about 2 wt % and about 15 wt % oxygenated co-surfactant.

In some embodiments, for the formulations above, other additives are present in an amount between about 1 wt % and about 30 wt %, between about 1 wt % and about 25 wt %, or between about 1 wt % and about 20 wt %. In some embodiments, the other additives comprise one or more salts and/or one or more acids.

It was unexpectedly found that in some embodiments, fluids comprising the disclosed microemulsions remain stable and exhibit low turbidity over a wide range of salinities and/or temperatures. As used herein, turbidity refers to the measure of cloudiness or haziness of a fluid caused by the presence of suspended particles in the fluid. In the case of a fluid comprising a microemulsion, turbidity serves as an indication of the stability of the microemulsion. A higher turbidity may be caused by phase separation of a less stable microemulsion upon dilution into high salinity and/or high temperature well conditions. Conversely, a low turbidity may be an indication that the microemulsion is more stable. Phase separation may decrease the efficacy of the microemulsion. Commonly-used units for measuring turbidity are Nephelometric Turbidity Units (NTU). A clear fluid corresponds to the fluid having a turbidity from 0 NTU to 15 NTU. A slightly hazy fluid corresponds to the fluid having a turbidity from 15 NTU to 100 NTU. A hazy fluid corresponds to the fluid having a turbidity from 100 NTU to 200 NTU. An opaque fluid corresponds to the fluid having a turbidity of 200 NTU or greater. Fluids comprising a microemulsion should have a turbidity in the range of slightly hazy or preferably clear to maximize the efficacy of the microemulsion.

Microemulsions disclosed herein demonstrate unexpectedly low turbidities even over a wide range of salinities. For example, in some embodiments, the microemulsions disclosed herein, upon dilution, have a turbidity of less than 100 NTU, of less than 50 NTU, or of less than 15 NTU, upon dilution at 2 gallons per thousand (gpt) in a brine having a TDS (total dissolved solids) value of from about 20,000 ppm up to about 310,000 ppm, when measured at room temperature one minute after dilution.

Likewise, the microemulsions disclosed herein may demonstrate unexpectedly low turbidities over a wide range of temperatures. For example, in some embodiments, the microemulsions, upon dilution at 2 gallons per thousand with a brine having a TDS value of about 240,000 ppm, have a turbidity value of less than 15 NTU, when measured at 75° F. using a turbidimeter, and a turbidity value of less than 15 NTU, when measured at 200° F. using a turbidimeter.

I-A. Aqueous Phase

Generally, the emulsion or the microemulsion comprises an aqueous phase. Generally, the aqueous phase comprises water. The water may be provided from any suitable source (e.g., sea water, fresh water, deionized water, reverse osmosis water, water from field production). The water may be present in any suitable amount. In some embodiments, the total amount of water present in the emulsion or the microemulsion is between about 10 wt % and about 70 wt %, between about 35 wt % and about 60 wt %, between about 10 wt % about 60 wt %, between about 35 wt % and about 55 wt %, between about 5 wt % and about 60 wt %, between about 10 wt % and about 55 wt %, or between about 15 wt % and about 45 wt %, versus the total emulsion or microemulsion composition.

I-B. Solvents

Generally, the emulsion or the microemulsion comprises a solvent. The solvent may be a single type of solvent or a combination of two or more types of solvent. The solvent may comprise an oleaginous hydrocarbon solvent; for example, the solvent may be a substance with a significant hydrophobic character with linear, branched, cyclic, bicyclic, saturated, or unsaturated structure, including terpenes and/or alkyl aliphatic carboxylic acid esters. The term "oleaginous" denotes an oily, non-polar liquid phase. In some embodiments, the solvent comprises terpene and/or methyl aliphatic carboxylic acid ester. In some embodiments, the terpene is a non-oxygenated terpene. In some embodiments, the terpene is d-limonene. In some embodiments, the terpene is dipentene. In some embodiments, the terpene is selected from the group consisting of d-limonene, nopol, alpha-terpineol, eucalyptol, dipentene, linalool, alpha-pinene, beta-pinene, and combinations thereof. As used herein, "terpene" refers to a single terpene compound or a blend of terpene compounds.

In some embodiments, the solvent is present in the emulsion or the microemulsion in an amount between about 1 wt % and about 25 wt %, between about 1 wt % and about 20 wt % or between about 9 wt % and about 17 wt %.

In some embodiments, d-limonene is present in the emulsion or the microemulsion in an amount between about 1 wt % and about 25 wt %, between about 1 wt % and about 20 wt % or between about 9 wt % and about 17 wt %. In some embodiments, methyl aliphatic carboxylic acid ester is present in the emulsion or the microemulsion in an amount between about 1 wt % and about 25 wt %, between about 1 wt % and about 20 wt % or between about 9 wt % and about 17 wt %. In some embodiments, a combination of d-limonene and methyl aliphatic carboxylic acid ester is present in the emulsion or the microemulsion in an amount between about 1 wt % and about 25 wt %, between about 1 wt % and about 20 wt % or between about 9 wt % and about 17 wt %. In some embodiments, the ratio of the d-limonene to the methyl aliphatic carboxylic acid ester is from about 1:0.01 to about 0.5:1 by weight, or from about 0.8:1 to about 1:0.8 by weight.

In some embodiments, the terpene is an oxygenated terpene, for example, a terpene comprising an alcohol, an aldehyde, an ether, and/or a ketone group. In some embodiments, the terpene comprises an alcohol group, otherwise referred to as a terpene alcohol. Non-limiting examples of terpene alcohols are linalool, geraniol, nopol, α-terpineol, and menthol. In some embodiments, the terpene comprises an ether-oxygen, for example, eucalyptol. In some embodiments, the terpene is a non-oxygenated terpene, for example, d-limonene or dipentene.

Terpenes are derived biosynthetically from units of isoprene. Terpenes may be generally classified as monoterpenes (e.g., having two isoprene units), sesquiterpenes (e.g., having 3 isoprene units), diterpenes, or the like. The term "terpenoid" also includes natural degradation products, such as ionones, and natural and synthetic derivatives, e.g., terpene alcohols, ethers, aldehydes, ketones, acids, esters, epoxides, and hydrogenation products (e.g., see Ullmann's Encyclopedia of Industrial Chemistry, 2012, pages 29-45, herein incorporated by reference). In some cases, the terpene is a naturally occurring terpene. In some cases, the terpene is a non-naturally occurring terpene and/or a chemically modified terpene (e.g., saturated terpene, terpene amine, fluorinated terpene, or silylated terpene). When terpenes are modified chemically, such as by oxidation or rearrangement of the carbon skeleton, the resulting compounds are generally referred to as terpenoids.

As used herein "alkyl aliphatic carboxylic acid ester" refers to a compound or a blend of compounds having the general formula:

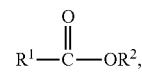

wherein $R^1$ is a $C_4$ to $C_{22}$ aliphatic group, including those bearing heteroatom-containing substituent groups, and $R^2$ is a $C_1$ to $C_6$ alkyl group. For example, where $R^2$ is —$CH_3$, the compound or blend of compounds is referred to as methyl aliphatic carboxylic acid ester, or methyl ester. Such alkyl aliphatic carboxylic acid esters may be derived from a fully synthetic process or from natural products, and thus comprise a blend of more than one ester.

I-C. Surfactants

Generally, the emulsion or microemulsion comprises a surfactant. In some embodiments, the emulsion or the microemulsion comprises a first surfactant and a second surfactant or co-surfactant. The term "surfactant" as used herein, is given its ordinary meaning in the art and refers to compounds having an amphiphilic structure which gives them a specific affinity for oil/water-type and water/oil-type interfaces which helps the compounds to reduce the free energy of these interfaces and to stabilize the dispersed phase of an emulsion or a microemulsion.

Generally, the surfactant comprises alkyl polyglycoside (APG). The surfactant may comprise one APG surfactant or a mixture of APG surfactants with different alkyl chains and/or degrees of polymerization (DP).

APGs are non-ionic surfactants having the following formula:

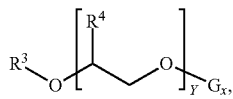

wherein $R^3$ is an aliphatic hydrocarbon group which can be straight chained or branched, saturated or unsaturated, and having from 6 to 16 carbon atoms; $R^4$ is H, —$CH_3$, or —$CH_2CH_3$; G is the residue of a reducing saccharide, for example, a glucose residue; Y is an average number of from about 0 to about 5; and X is an average degree of polymerization (DP) of from about 1 to about 4. The DP is an average of the number of glycose groups attached to the molecule. As used herein, reference to the surfactant comprising APG refers both to where a single APG species is present and to where a mixture of APG species with different alkyl chains and/or degrees of polymerization (DP) are present. The number of carbon atoms in the aliphatic hydrocarbon group $R^3$ is referred to as the carbon chain length of the APG surfactant. In some embodiments, the APG surfactant comprises one or more species having a carbon chain length between 6 and 16 carbon atoms. In some embodiments, the number average carbon chain length of the APG surfactant is between 6 and 16 carbon atoms.

In some embodiments, alkyl polyglycoside surfactant is present in the emulsion or the microemulsion in an amount between about 10 wt % and about 25 wt % or between about 16 wt % and about 24 wt %. Other values are also possible. In some embodiments, specific surfactant components are excluded from the emulsion or the microemulsion. For example, the surfactant of the emulsion or the microemulsion may exclude an ethoxylated castor oil. In some embodiments the surfactant component of the emulsion or the microemulsion consists of or consists essentially of APG surfactant. That is, no other surfactants are present in the emulsion or the microemulsion, or they are present in only a negligible amount.

It was unexpectedly found that use of APG surfactant, in some embodiments, increased the stability of the emulsion or the microemulsion over a wide range of temperatures and/or salinities, when incorporated into the emulsion or the microemulsion formulations disclosed herein. Such emulsions or microemulsions may maintain stability even when subjected to a wide range of temperatures due to the environmental conditions present at the subterranean formation and/or reservoir.

I-D. Alcohol

Generally, the emulsion or microemulsion comprises an alcohol. The alcohol may function as a co-solvent. The alcohol may be selected from alcohols having from 1 to 8 carbon atoms, and combinations thereof. The alcohol may be selected from the group consisting of butanol, pentanol, amyl alcohol, and combinations thereof. In some embodiments the alcohol is selected from the group consisting of butanol, amyl alcohol, and combinations thereof. In some embodiments, the alcohol comprises butanol. In some embodiments, the alcohol comprises amyl alcohol. In some embodiments, the alcohol comprises a combination of butanol and amyl alcohol.

It was unexpectedly found that the presence of certain alcohols in particular, for example, butanol or amyl alcohol, resulted in markedly improved stability of the emulsion or the microemulsion over a range of temperatures and salinities. However, it is understood that alternative alcohols or oxygenated co-solvents may still yield emulsions or microemulsions exhibiting sufficient stability.

In some embodiments, the alcohol is present in the emulsion or the microemulsion in an amount between about 2 wt % and about 15 wt % or between about 4 wt % and about 9 wt %. In some embodiments, butanol is present in the emulsion or the microemulsion in an amount between about 2 wt % and about 15 wt % or between about 4 wt % and about 9 wt %. In some embodiments, amyl alcohol is present in the emulsion or the microemulsion in an amount between about 2 wt % and about 15 wt % or between about 4 wt % and about 9 wt %. In some embodiments, a combination of butanol and amyl alcohol is present in the emulsion or the microemulsion in an amount between about 2 wt % and about 15 wt % or between about 4 wt % and about 9 wt %.

I-E. Additives

In some embodiments, the emulsion or microemulsion may comprise one or more additives in addition to the components discussed above. In some embodiments, the additive is a freezing point depression agent (e.g., propylene glycol). In some embodiments, the additive is a demulsifier. The demulsifier aids in preventing the formulation of an emulsion between a treatment fluid and crude oil. Some non-limiting examples of demulsifiers include polyoxyethylene (50) sorbitol hexaoleate. Other potential additives include a proppant, a scale inhibitor, a friction reducer, a biocide, a corrosion inhibitor, a buffer, a viscosifier, an oxygen scavenger, a clay control additive, a paraffin control additive, an asphaltene control additive, an acid, an acid precursor, or a salt.

Additional additive may be present in the emulsion or the microemulsion in any suitable amount. In some embodiments, the one or more additional additives are present in an amount between about 0.5 wt % and about 30 wt %, between about 1 wt % and about 40 wt %, between about 0 wt % and about 25 wt %, between about 1 wt % and about 25 wt %, between about 1 wt % and about 20 wt %, between about 3 wt % and about 20 wt %, or between about 8 wt % and about 16 wt %, versus the total emulsion or microemulsion composition. In some embodiments a freezing point depression agent is present in the emulsion or microemulsion in an amount between about 10 wt % and about 15 wt %. In some embodiments, a demulsifier is present in the emulsion or microemulsion in an amount between about 4 wt % and about 8 wt %.

In some embodiments, the emulsion or the microemulsion comprises a freezing point depression agent. The emulsion or the microemulsion may comprise a single freezing point depression agent or a combination of two or more freezing point depression agents. The term "freezing point depression agent" is given its ordinary meaning in the art and refers to a compound which is added to a solution to reduce the freezing point of the solution. That is, a solution comprising the freezing point depression agent has a lower freezing point as compared to an essentially identical solution not comprising the freezing point depression agent. Those of ordinary skill in the art will be aware of suitable freezing point depression agents for use in the emulsions or the microemulsions described herein. Non-limiting examples of freezing point depression agents include primary, secondary, and tertiary alcohols with between 1 and 20 carbon atoms. In addition to the freezing point depression agent, the emulsion or the microemulsion may comprise other additives. Further non-limiting examples of other additives include proppants, scale inhibitors, friction reducers, biocides, corrosion inhibitors, buffers, viscosifiers, oxygen scavengers, clay control additives, paraffin control additives, asphaltene control additives acids, acid precursors, and salts.

Non-limiting examples of proppants (e.g., propping agents) include grains of sand, glass beads, crystalline silica (e.g., quartz), hexamethylenetetramine, ceramic proppants (e.g., calcined clays), resin coated sands, and resin coated ceramic proppants. Other proppants are also possible and will be known to those skilled in the art.

Non-limiting examples of scale inhibitors include one or more of methyl alcohol, organic phosphonic acid salts (e.g., phosphonate salt, aminopolycarboxlic acid salts), polyacrylate, ethane-1,2-diol, calcium chloride, and sodium hydroxide. Other scale inhibitors are also possible and will be known to those skilled in the art.

Non-limiting examples of friction reducers include oil-external emulsions of polymers with oil-based solvents and an emulsion-stabilizing surfactant. The emulsions may include Natural-based polymers like guar, cellulose, xanthan, proteins, polypeptides or derivatives of same or synthetic polymers like polyacrylamide-co-acrylic acid (PAM-AA), polyethylene oxide, polyacrylic acid, and other copolymers of acrylamide and other vinyl monomers. For a list of non-limiting examples, see U.S. Pat. No. 8,865,632, which is incorporated herein by reference. Other common drag-reducing additives include dispersions of natural- or synthetic polymers and copolymers in saline solution and dry natural- or synthetic polymers and copolymers. These polymers or copolymers may be nonionic, zwitterionic, anionic, or cationic depending on the composition of polymer and pH of solution. Other friction reducers are also possible and will be known to those skilled in the art.

Non-limiting examples of biocides include didecyl dimethyl ammonium chloride, gluteral, Dazomet, bronopol, tributyl tetradecyl phosphonium chloride, tetrakis (hydroxymethyl) phosphonium sulfate, AQUCAR®, UCAR-CIDE®, glutaraldehyde, sodium hypochlorite, and sodium hydroxide. Other biocides are also possible and will be known to those skilled in the art.

Non-limiting examples of corrosion inhibitors include quaternary ammonium compounds, thiourea/formaldehyde copolymers, and propargyl alcohol. Other corrosion inhibitors are also possible and will be known to those skilled in the art.

Non-limiting examples of buffers include acetic acid, acetic anhydride, potassium hydroxide, sodium hydroxide, and sodium acetate. Other buffers are also possible and will be known to those skilled in the art.

Non-limiting examples of viscosifiers include polymers like guar, cellulose, xanthan, proteins, polypeptides or derivatives of same or synthetic polymers like polyacrylamide-co-acrylic acid (PAM-AA), polyethylene oxide, polyacrylic acid, and other copolymers of acrylamide and other vinyl monomers. Other viscosifiers are also possible and will be known to those skilled in the art.

Non-limiting examples of oxygen scavengers include sulfites and bisulfites. Other oxygen scavengers are also possible and will be known to those skilled in the art.

Non-limiting examples of clay control additives include quaternary ammonium chloride and tetramethylammonium chloride. Other clay control additives are also possible and will be known to those skilled in the art.

Non-limiting examples of paraffin control additives and asphaltene control additives include active acidic copolymers, active alkylated polyester, active alkylated polyester amides, active alkylated polyester imides, aromatic naphthas, and active amine sulfonates. Other paraffin control additives and asphaltene control additives are also possible and will be known to those skilled in the art.

In some embodiments, the emulsion or the microemulsion comprises an acid or an acid precursor. For example, the emulsion or the microemulsion may comprise an acid when used during acidizing operations. In some embodiments, the APG surfactant used is alkaline and an acid (e.g., HCl) used to adjust the pH of the emulsion or the microemulsion to neutral. The emulsion or the microemulsion may comprise a single acid or a combination of two or more acids. For example, in some embodiments, the acid comprises a first type of acid and a second type of acid. Non-limiting examples of acids or di-acids include hydrochloric acid, acetic acid, formic acid, succinic acid, maleic acid, malic acid, lactic acid, and hydrochloric-hydrofluoric acids. In some embodiments, the emulsion or the microemulsion comprises an organic acid or organic di-acid in the ester (or di-ester) form, whereby the ester (or diester) is hydrolyzed in the wellbore and/or reservoir to form the parent organic acid and an alcohol in the wellbore and/or reservoir. Non-limiting examples of esters or di-esters include isomers of methyl formate, ethyl formate, ethylene glycol diformate, $\alpha,\alpha$-4-trimethyl-3-cyclohexene-1-methylformate, methyl lactate, ethyl lactate, $\alpha,\alpha$-4-trimethyl 3-cyclohexene-1-methyllactate, ethylene glycol dilactate, ethylene glycol diacetate, methyl acetate, ethyl acetate, $\alpha,\alpha$,-4-trimethyl-3-cyclohexene-1-methylacetate, dimethyl succinate, dimethyl maleate, di($\alpha,\alpha$-4-trimethyl-3-cyclohexene-1-methyl)succinate, 1-methyl-4-(1-methylethenyl)-cyclohexylformate, 1-methyl-4-(1-ethylethenyl)-cyclohexylactate, 1-methyl-4-(1-methylethenyl)-cyclohexylacetate, and di(1-methy-4-(1-methylethenyl)-cyclohexyl)-succinate.

In some embodiments, the emulsion or the microemulsion comprises a salt. The presence of the salt may reduce the amount of water needed as a carrier fluid, and in addition, may lower the freezing point, of the emulsion or the microemulsion. The emulsion or the microemulsion may comprise a single salt or a combination of two or more salts. For example, in some embodiments, the salt comprises a first type of salt and a second type of salt. Non-limiting examples of salts include salts comprising K, Na, Br, Cr, Cs, or Li, for example, halides of these metals, including NaCl, KCl, $CaCl_2$, and $MgCl_2$.

In some embodiments, the emulsion or the microemulsion comprises a clay control additive. The emulsion or the microemulsion may comprise a single clay stabilizer or a combination of two or more clay stabilizers. For example, in some embodiments, the clay control additive comprises a first type of clay control additive and a second type of clay control additive. Non-limiting examples of clay control additives include the salts above, polymers (PAC, PHPA, etc), glycols, sulfonated asphalt, lignite, sodium silicate, and choline chloride.

I-F. Formation and Use of Emulsions or Microemulsions

In some embodiments, the components of the microemulsion and/or the amounts of the components are selected such that the microemulsion is stable over a wide-range of temperatures, as demonstrated, for example, by a turbidity below a certain threshold (e.g., 100 NTU, 50 NTU, or 15 NTU).

In some embodiments, the components of the microemulsion and/or the amounts of the components are selected such that the microemulsion is stable over a wide-range of salinities. For example, the microemulsion may exhibit stability between about 20,000 ppm TDS and about 310,000 ppm TDS.

The emulsions and the microemulsions described herein may be formed using methods known to those of ordinary skill in the art. In some embodiments, the aqueous and non-aqueous phases may be combined (e.g., the water and the solvent(s)), followed by addition of a surfactant and co-surfactant and optional additives (e.g., a freezing point depression agent or a demulsifier) and agitation. The strength, type, and length of the agitation may be varied as known in the art depending on various factors including the components of the emulsions or the microemulsion, the quantity of the emulsions or the microemulsion, and the resulting type of emulsion or microemulsion formed. For example, for small samples, a few seconds of gentle mixing can yield an emulsion or a microemulsion, whereas for larger samples, longer agitation times and/or stronger agitation may be required. Agitation may be provided by any suitable source, for example, a vortex mixer, a stirrer (e.g., magnetic stirrer), etc.

Any suitable method for injecting the emulsion or the microemulsion (e.g., a diluted microemulsion) into a wellbore may be employed. For example, in some embodiments, the emulsion or the microemulsion, optionally diluted, may be injected into a subterranean formation by injecting it into a well or wellbore in the zone of interest of the formation and thereafter pressurizing it into the formation for the selected distance. Methods for achieving the placement of a selected quantity of a mixture in a subterranean formation are known in the art. The well may be treated with the emulsion or the microemulsion for a suitable period of time. The emulsion or the microemulsion and/or other fluids may be removed from the well using known techniques, including producing the well.

It should be understood, that in embodiments where an emulsion or a microemulsion is said to be injected into a wellbore, that the emulsion or the microemulsion may be diluted and/or combined with other liquid component(s) prior to and/or during injection (e.g., via straight tubing, via coiled tubing, etc.). For example, in some embodiments, the emulsion or the microemulsion is diluted with an aqueous carrier fluid (e.g., water, brine, sea water, fresh water, or a well-treatment fluid (e.g., an acid, a fracturing fluid comprising polymers, produced water, sand, slickwater, etc.)) prior to and/or during injection into the wellbore. In some embodiments, a composition for injecting into a wellbore is provided comprising an emulsion or a microemulsion as described herein and an aqueous carrier fluid, wherein the emulsion or the microemulsion is present in an amount between about 0.1 and about 50 gallons per thousand gallons (gpt) per dilution fluid, between about 0.1 and about 100 gpt, between about 0.5 and about 10 gpt, between about 0.5 and about 2 gpt, or between about 1 gpt and about 4 gpt.

II. Applications of the Emulsions and/or Microemulsions Relating to the Life Cycle of an Oil/Gas Well The emulsions and microemulsions described herein may be used in various aspects of the life cycle of an oil and/or gas well, including, but not limited to, drilling, mud displacement, casing, cementing, perforating, stimulation, remediation, and enhanced oil recovery/improved oil recovery, etc. Inclusion of an emulsion or a microemulsion into the fluids typically employed in these processes, for example, fracturing fluids, drilling fluids, mud displacement fluids, casing fluids, cementing fluids, perforating fluid, stimulation fluids, kill fluids, etc., results in many advantages as compared to use of the fluid alone.

As will be known to those skilled in the art, generally the completion of the formation of wellbore includes stimulation and/or re-fracturing processes. The term "stimulation" generally refers to the treatment of geological formations to improve the recovery of liquid hydrocarbons (e.g., formation crude oil and/or formation gas). The porosity and permeability of the formation determine its ability to store hydrocarbons, and the facility with which the hydrocarbons can be extracted from the formation. Common stimulation techniques include well fracturing (e.g., fracturing, hydraulic fracturing), high rate water pack, and acidizing (e.g., fracture acidizing, matrix acidizing) operations.

Non-limiting examples of fracturing operations include hydraulic fracturing, which is commonly used to stimulate low permeability geological formations to improve the recovery of hydrocarbons. The process can involve suspending chemical agents in a stimulation fluid (e.g., fracturing fluid) and injecting the fluid down a wellbore. The fracturing fluid may be injected at high pressures and/or at high rates into a wellbore. However, the assortment of chemicals pumped down the well can cause damage to the surrounding formation by entering the reservoir material and blocking pores. For example, one or more of the following may occur: wettability reversal, emulsion blockage, aqueous-filtrate blockage, mutual precipitation of soluble salts in wellbore-fluid filtrate and formation water, deposition of paraffins or asphaltenes, condensate banking, bacterial plugging, and/or gas breakout. In addition, fluids may become trapped in the formation due to capillary end effects in and around the vicinity of the formation fractures. The addition of an emulsion or a microemulsion in the fracturing fluid may have many advantages as compared to the use of a fracturing fluid alone, including, for example, maximizing the transfer and/or recovery of injected fluids, increasing oil and/or gas recovery, and/or other benefits described herein.

Non-limiting examples of acidizing operations include the use of water-based fluids to remove drilling fluids and particles remaining in the wellbore to permit optimal flow feeding into the wellbore (e.g., matrix acidizing). Matrix acidizing generally refers to the formation of wormholes (e.g., pores or channels through which oil, gas, and/or other fluids can flow) through the use of a fluid (e.g., acidic stimulation fluid) comprising, for example, an acid, wherein the wormholes are continuous channels and holes formed in the reservoir of a controlled size and depth. The addition of an emulsion or a microemulsion to the stimulation fluid may have many advantages as compared to the use of a stimulation fluid alone.

Fracture acidizing generally refers to the use of an acid to extend fractures formed by the injection of treatment fluid at high-pressure (e.g., fracturing). The addition of an emulsion or a microemulsion to the stimulation fluid may have advantages as compared to the use of a stimulation fluid alone, including, for example, increasing the removal of fracturing fluid skin (e.g., fluid and solids from the reservoir which may block optimal flow of the wellbore) from the fractures allowing for more effective acid treatment.

As will be known to those skilled in the art, stimulation fluids (e.g., acidizing fluids, fracturing fluids, etc.) may be injected into the wellbore to assist in the removal of leftover drilling fluids or reservoir materials. Non-limiting examples of stimulation fluids (e.g., as an acidizing fluid) include water and hydrochloric acid (e.g., 15% HCl in water). In some embodiments, the acid is partially or completely consumed after reacting with carbonates in the reservoir. Further non-limiting examples of stimulation fluids include conventional fluids (e.g., gelling agents, gelling agents comprising crosslinking agents such as borate, zirconate, and/or titanate), water fracture fluids (e.g., friction reducers, gelling agents, viscoelastic surfactants), hybrid fluids (e.g., friction reducers, gelling agents, viscoelastic surfactants, and combinations thereof), energized fluids (e.g., foam generating energizers comprising nitrogen or carbon dioxide), acid fracture fluids (e.g., gelled acid base fluids), gas fracture fluids (e.g., propane), and matrix acidizing fluids (e.g., an acid).

In some embodiments, the stimulation fluid comprises a viscosifier (e.g., guar gum) and/or a bridging agent (e.g., calcium carbonate, size salt, oil-soluble resins, mica, ground cellulose, nutshells, and other fibers). In some embodiments, removal of leftover drilling fluids or reservoir fluids refers to the breakdown and removal of a near-wellbore skin (e.g., fluid and solids from the reservoir which may block optimal flow into the wellbore). Non-limiting examples of skin materials include paraffin, asphaltene, drilling mud components (e.g., barite, clays), non-mobile oil in place, and fines (e.g., which may block pores in the reservoir material). The addition of an emulsion or a microemulsion to the acidizing fluid may have many advantages as compared to the use of an acidizing fluid alone, including, for example, increasing the breakdown of the skin into smaller components to be more easily removed by flow from the wellbore, increasing oil and/or gas recovery, and/or other benefits described herein.

In addition to some of the benefits described above, in some embodiments, incorporation of an emulsion or a microemulsion into a stimulation fluid can aid in reducing fluid trapping, for example, by reducing capillary pressure and/or minimizing capillary end effects, as compared to the use of a stimulation fluid alone. Capillary pressure is defined by $$Pc = 2 * \gamma * \cos(\theta) / r$$

Where $\gamma$ is the interfacial tension, $\theta$ is the contact angle, and $r$ is the radius of the capillary. The capillary pressure is the pressure across an interface in a capillary or pore. It may refer to a liquid/gas (or water/air) interface, or to a liquid/liquid (water/crude oil) interface. If the solid surface is water-wet ($\theta < 90°$), and the interfacial tension is moderate (for example, 5 mN/m), the capillary pressure will resist flow of the oil phase. Lowering the capillary pressure, by either modifying wettability to a value close to $\theta = 90°$, or decreasing the interfacial tension, reduces the resistance to flow and increases hydrocarbon production. Some of the wetting phase (which may be either water or oil) may be trapped in dead end pores or a narrow pore throat and is difficult to mobilize. This is called the capillary end effect.

Reducing capillary pressure and/or minimizing capillary end effects is beneficial, because it decreases resistance to flow of oil (sometimes called water blocks) and increases production of hydrocarbon. In addition, incorporation of an emulsion or a microemulsion into stimulation fluids can promote increased flow back of aqueous phases following well treatment, increasing production of liquid and/or gaseous hydrocarbons, and/or increasing the displacement of residual fluids (e.g., drilling fluids, etc.) by formation crude oil and/or formation gas. Other non-limiting advantages as compared to the use of a stimulation fluid alone, include increasing the amount of water extracted from the reservoir, increasing the amount or oil and/or gas extracted from the reservoir, more uniformly distributing the acid along the surface of the wellbore and/or reservoir, improving the formation of wormholes (e.g., by slowing down the reaction rate to create deeper and more extensive wormholes during fracture acidizing). In certain embodiments, the addition of an emulsion or a microemulsion increases the amount of hydrocarbons transferred from the reservoir to fluids injected into the reservoir during hydraulic fracturing.

In some embodiments, the stimulation fluid comprises an emulsion or a microemulsion as described herein wherein the emulsion or the microemulsion is present in an amount between about 0.5 gpt and about 200 gpt of stimulation fluid, or between about 0.5 gpt and about 100 gpt, between about 0.5 gpt and about 50 gpt, between about 1 gpt and about 50 gpt, between about 1 gpt and about 20 gpt, between about 2 gpt and about 20 gpt, between about 2 gpt and about 10 gpt, between about 2 gpt and about 5 gpt, or between about 5 gpt and about 10 gpt. In some embodiments, the emulsion or the microemulsion is present in an amount between about 2 gpt and about 5 gpt of stimulation fluid. In some embodiments, the stimulation fluid contains at least about 0.5 gpt, at least about 1 gpt, at least about 2 gpt, at least about 4 gpt, at least about 10 gpt, at least about 20 gpt, at least about 50 gpt, at least about 100 gpt, or at least about 200 gpt of an emulsion or a microemulsion. In some embodiments, the stimulation fluid contains less than or equal to about 200 gpt, less than or equal to about 100 gpt, less than or equal to about 50 gpt, less than or equal to about 20 gpt, less than or equal to about 10 gpt, less than or equal to about 4 gpt, less than or equal to about 2 gpt, less than or equal to about 1 gpt, or less than or equal to about 0.5 gpt of an emulsion or a microemulsion.

In some embodiments, refracturing, or the process of repeating the above stimulation processes, is further improved by the addition of an emulsion or a microemulsion to the stimulation fluid.

IV. Definitions

For convenience, certain terms employed in the specification, examples, and appended claims are listed here.

The terms "emulsion" and "microemulsion" should be understood to include emulsions or microemulsions that have a water continuous phase, or that have an oil continuous phase, or microemulsions that are bicontinuous or multiple continuous phases of water and oil.

As used herein, the term "emulsion" is given its ordinary meaning in the art and refers to dispersions of one immiscible liquid in another, in the form of droplets, with diameters approximately in the range of about 100 to about 10,000 nanometers (nm). Emulsions may be thermodynamically unstable and/or require high shear forces to induce their formation.

As used herein, the term "microemulsion" is given its ordinary meaning in the art and refers to dispersions of one immiscible liquid in another, in the form of droplets, with diameters approximately in the range of about between about 10 to about 300 nanometers. Microemulsions are clear or transparent because they contain domains smaller than the wavelength of visible light. In addition, microemulsions are homogeneous, thermodynamically stable, single phases, and form spontaneously, and thus, differ markedly from thermodynamically unstable emulsions, which generally depend upon intense mixing energy for their formation. Microemulsions may be characterized by a variety of advantageous properties including, by not limited to, (i) clarity, (ii) very small particle size, (iii) ultra-low interfacial tensions, (iv) the ability to combine properties of water and oil in a single homogeneous fluid, (v) shelf life stability, (vi) ease of preparation; (vii) compatibility; and (viii) solvency.

In some embodiments, the microemulsions described herein are stabilized microemulsions that are formed by the combination of a solvent-surfactant blend with an appropriate oil-based or water-based carrier fluid. Generally, the microemulsion forms upon simple mixing of the components without the need for high shearing generally required in the formation of emulsions. In some embodiments, the microemulsion is a thermodynamically stable system, and the droplets remain finely dispersed over time. In some cases, the average droplet size ranges from about 10 nm to about 300 nm.

As used herein, the term "co-solvent" refers to a glycol or an alcohol having 1 to 8 carbon atoms, that when incorporated in an emulsion or microemulsion composition, increases the temperature, salinity, and composition stability of the microemulsion to form the microemulsion.

As used herein, the term "co-surfactant" refers to a low-molecular-weight surfactant, e.g., a lower fatty alcohol, which acts in conjunction with a surfactant to form an emulsion or microemulsion.

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito: 1999, the entire contents of which are incorporated herein by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

The term "aliphatic," as used herein, includes both saturated and unsaturated, nonaromatic, straight chain (i.e. unbranched), branched, acyclic, and cyclic (i.e. carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkane" is given its ordinary meaning in the art and refers to a saturated hydrocarbon molecule. The term "branched alkane" refers to an alkane that includes one or more branches, while the term "unbranched alkane" refers to an alkane that is straight-chained. The term "cyclic alkane" refers to an alkane that includes one or more ring structures, and may be optionally branched. The term "acyclic alkane" refers to an alkane that does not include any ring structures, and may be optionally branched.

These and other aspects of the present invention will be further appreciated upon consideration of the following Examples, which are intended to illustrate certain particular embodiments of the invention but are not intended to limit its scope, as defined by the claims.

EXAMPLES

Example 1

Experimental Procedure

For the following Examples 2-5, the procedure for determining displacement of residual aqueous treatment fluid by a crude oil was as follows. Two 25 cm long, 2.5 cm diameter capped glass chromatography columns were packed with 40 grams of 100 mesh sand. The columns were left open on one end and a PTFE insert containing a recessed bottom, 3.2 mm diameter outlet, and a nipple was placed into the other end. Prior to placing the inserts into the columns, 3 cm diameter filter paper discs (Whatman, #40) were pressed firmly into the recessed bottom of the insert to prevent leakage of sand. Two inch long pieces of vinyl tubing were placed onto the nipples of the inserts and clamps were fixed in place on the tubing prior to packing. The sand was added to the columns in a stepwise fashion with the brine to be studied. The sand was packed using a hand-held vibrating column packer in between each stepwise addition until all of the material (40-45 grams) had been added. The amount of fluid used in the process was tracked and the pore volume of the sand pack was calculated for both columns. Five pore volumes of the treatment were passed through the first column, collected from the first column, then passed through the second column. After the last pore volume was passed through the first and second columns, the level of the aqueous phase was adjusted exactly to the top of sand bed and crude oil was added on top of the sand bed to a height of 5 cm oil column above the bed. Once the setup was assembled, the clamps were released from the tubing, and a timer was started. Throughout the experiment the level of crude oil was monitored and kept constant at the 5 cm height above the bed. Crude oil was added as necessary, to ensure a constant hydrostatic head in the columns. Portions of effluent coming from the columns were collected into plastic beakers over measured time intervals. The amount of fluid was monitored. The experiment was conducted for two hours after which time steady-state conditions were typically reached.

Example 2

This example describes an experiment for determining the displacement of residual aqueous treatment fluid by crude oil to test the performance of a microemulsion comprising APG surfactant [Microemulsion A], in which the microemulsion is diluted in different brines (2% KCl, 12% API brine, and 24% API brine and produced water from the Bakken formation (310,000 ppm TDS)). Microemulsion A used in this example was prepared using 51.4 wt % water; 16.8 wt % d-limonene as a solvent; 23.4 wt % APG surfactant; and 8.4 wt % butanol as an alcohol functioning as a co-solvent. The APG surfactant used in this example had a $C_{8-16}$ alkyl chain and a degree of polymerization (DP) equal to 1.5.

Two gallons per thousand (gpt) dilutions were prepared in the different brines and tested. Table 1 shows the results of displacement of residual aqueous treatment fluid by crude oil using the experimental procedure outlined in Example 1. Microemulsion A performs very well at all salinities for both columns. Table 1 presents the percentages of residual aqueous fluid displaced from the column as measured after 120 minutes. The residual aqueous fluid was displaced by crude oil (30.9° API gravity; 3.2% asphaltenes; 4.32% paraffin) for Microemulsion A diluted at 2 gpt in 2% KCl (20,000 ppm TDS), 12% API brine (120,000 ppm TDS) and 24% API brine (240,000 ppm TDS).

As shown in Table 1, the results indicate that Microemulsion A exhibited a robust performance with regard to displacement of residual aqueous treatment fluid by crude oil over a surprisingly wide range of salinity conditions.

TABLE 1

| Brine | 1st column | 2nd column |
|---|---|---|
| 2% KCl | 83% | 77% |
| 12% API brine | 92% | 92% |
| 24% API brine | 92.5% | 92.5% |

Example 3

Experiments to determine the displacement of residual aqueous treatment fluid by crude oil were conducted to test the performance of two microemulsions, one made with APG surfactant ($C_{8-16}$ alkyl chain and DP equal to 1.5) [Microemulsion B] and the other one with an alkyl ethoxylate non-ionic surfactant ($C_{12-15}E_7$) [Microemulsion C]. All other components of Microemulsions B and C were the same. Microemulsion B used in this example was prepared using 36.0 wt % water; 8.16 wt % d-limonene and 8.16 wt % methyl ester as a solvent; 22.7 wt % APG surfactant; 6.7 wt % amyl alcohol functioning as a co-solvent; 13 wt % propylene glycol as a freezing point depression agent, and 5.25 wt % demulsifier. Microemulsion C was prepared using 36.0 wt % water; 8.16 wt % d-limonene, and 8.16 wt % methyl ester as a solvent; 22.7 wt % non-ionic surfactant ($C_{12-15}E_7$) as a surfactant; 6.7 wt % amyl alcohol functioning as a co-solvent; and 13 wt % propylene glycol as a freezing point depression agent, and 5.25 wt % demulsifier. Two gpt dilutions of Microemulsions B and C were prepared in the Bakken C water (310,000 ppm TDS) and tested. The methyl ester used in this example was a $C_{10}$ to a $C_{16}$ aliphatic carboxylic acid ester with one degree of unsaturation in the aliphatic group. The demulsifier was polyoxyethylene (50) sorbitol hexaoleate.

Table 2 shows the results of displacement of residual aqueous treatment fluid by crude oil (32.4° API gravity; 3.4% asphaltenes; 4.63% paraffin) for Microemulsions B and C diluted at 2 gpt in Bakken C water. Microemulsion C shows a much lower performance in the second column compared to Microemulsion B, possibly due to the salting out of the $C_{12-15}E_7$ surfactant, demonstrating the superiority of Microemulsion B comprising APG surfactant.

TABLE 2

| | Microemulsion B | Microemulsion C |
|---|---|---|
| Column 1 | 92.5% | 92.5% |
| Column 2 | 96.8% | 47.8% |

Example 4

Experiments to determine the displacement of residual aqueous treatment fluid by crude oil were conducted to test the performance of a microemulsion comprising an APG surfactant ($C_{8-16}$ alkyl chain and DP equal to 1.5) [Microemulsion A] compared to a standard, non-ionic terpene microemulsion without an APG surfactant [Microemulsion D], that embodies the prior art. Two gpt of Microemulsion A and Microemulsion D were diluted in Bakken C water.

Table 3 shows the results of displacement of residual aqueous treatment fluid by crude oil. As shown in Table 3, Microemulsion D loses all performance in the second column, demonstrating the unexpected benefit of using a microemulsion comprising an APG surfactant [Microemulsion A] for enhanced displacement of residual aqueous treatment fluid. Table 3 shows the results of displacement of residual aqueous treatment fluid by a crude oil (30.9° API gravity; 3.2% asphaltenes; 4.32% paraffin) for Microemulsion A and Microemulsion D diluted at 2 gpt in Bakken C water.

TABLE 3

| | Microemulsion A | Microemulsion D |
|---|---|---|
| Column 1 | 95.4% | 76% |
| Column 2 | 93% | 7.7% |

Example 5

Experiments to determine the displacement of residual aqueous treatment fluid by crude oil were conducted to test the performance of two APG surfactant microemulsions formulated using different amounts of APG surfactant and d-limonene (Microemulsions F and G). Microemulsion F used in this example was prepared using 62.6 wt % water; 17.33 wt % d-limonene as a first solvent; 16.24 wt % APG surfactant; and 3.47 wt % isopropyl alcohol and 0.36 wt % octanol as a co-solvent.

Microemulsion G used in this example was prepared using 69.3 wt % water; 9.23 wt % d-limonene as a first solvent; 16.2 wt % APG surfactant; and 5.27 wt % isopropyl alcohol as a co-solvent.

Both Microemulsions F and G gave a displacement of residual aqueous treatment fluid of 90% using a medium crude oil (30.9° API gravity; 3.2% asphaltenes; 4.32% paraffin) and 15% API brine in the first column. The APG surfactant used in Microemulsions F and and G had a $C_{10-16}$ alkyl chain and a DP equal to 1.4. This example shows that microemulsions comprising a different APG surfactant and amounts of terpene solvent from 9.23 wt % to 17.33 wt % surprisingly provide superior displacement of residual aqueous treatment fluid in 15% API brine compared with Microemulsions C and D, which do not contain APG surfactant.

Example 6

Different microemulsions comprising APG surfactant were diluted into aqueous brines and their turbidity was measured at room temperature one minute after the dilution using a turbidimeter. The turbidity is expressed in Nephelometric Turbidity Units (NTUs). Photographs were taken of solutions at various turbidities, and a scale was established that relates the clarity metrics "Clear", "Slightly Hazy", "Hazy", and "Opaque" to certain ranges of NTUs. "Clear" corresponds to a turbidity from 0 NTU to 15 NTU. "Slightly Hazy" corresponds to a turbidity from 15 NTU to 100 NTU. "Hazy" corresponds to a turbidity from 100 NTU to 200 NTU. "Opaque" corresponds to a turbidity of 200 NTU or greater.

The turbidity of 2 gpt of Microemulsions B, C and H in different brines was measured. Microemulsion B was made with amyl alcohol and Microemulsion H was made with alpha-terpineol. The choice of the co-solvent is very important to obtain a water clear dilution. Microemulsion H used in this example was prepared using 36.0 wt % water; 8.16 wt % d-limonene and 8.16 wt % methyl ester as a solvent; 22.7 wt % APG surfactant; 6.7 wt % alpha-terpineol as an alcohol functioning as a co-solvent; 13.05 wt % propylene glycol as a freezing point depression agent; and 5.25 wt % demulsifier. The APG surfactant used in Microemulsion H had a $C_{8-16}$ alkyl chain and a DP equal to 1.5.

Table 4 shows the turbidity measurements of 2 gpt dilutions of Microemulsions B, C, and H in different brines (2% KCl, 12% API brine, 24% API brine and Bakken C water). Microemulsion B which incorporates APG surfactant and amyl alcohol demonstrated robust performance throughout salinities ranging from about 20,000 ppm TDS to about 310,000 ppm TDS, maintaining a turbidity of less than 15 NTU for all salinities in this range.

Microemulsion H, which incorporated alpha-terpinol rather than amyl alcohol as the co-solvent, had a turbidity in the slightly hazy range demonstrating instability of the microemulsion at different salinities, and showing a less robust performance than Microemulsion B. The difference in performance between Microemulsion B and Microemulsion H demonstrates the criticality of using certain alcohols as co-solvents as compared to other alcohols. Butanol also shows strong performance as a co-solvent as demonstrated through Microemulsion A referenced in Examples 2 and 4. Microemulsion C which did not include APG surfactant, also showed poor dilution in brines compared to Microemulsion B, demonstrating the criticality of using APG surfactant.

TABLE 4

| | 2% KCl | 12% API brine | 24% API brine | Bakken C water |
|---|---|---|---|---|
| Microemulsion B | 5.33 NTU | 2.50 NTU | 10.40 NTU | 1.72 NTU |
| Microemulsion C | 175 NTU | 158 NTU | 98.7 NTU | 171 NTU |
| Microemulsion H | 30.40 NTU | 36.80 NTU | 59.80 NTU | 97.70 NTU |

Example 7

The turbidity of Microemulsions I and Microemulsion J were measured through a procedure like that described in Example 6. Microemulsion I and Microemulsion J differed only in the alcohol used. Amyl alcohol was used for Microemulsion I and octanol was used for Microemulsion J.

Microemulsion I used in this example was prepared using 35.35 wt % water; 8.085 wt % d-limonene and 8.085 wt % methyl ester as a solvent; 22.26 wt % APG surfactant ($C_{8-16}$ alkyl chain and DP equal to 1.5); 8.18 wt % amyl alcohol as an alcohol functioning as a co-solvent; 12.86 wt % propylene glycol as a freezing point depression agent; and 5.18 wt % demulsifier. The demulsifier was polyoxyethylene (50) sorbitol hexaoleate.

Microemulsion J used in this example was prepared using 35.35 wt % water; 8.085 wt % d-limonene and 8.085 wt % methyl ester as solvent; 22.26 wt % APG surfactant ($C_{8-16}$ alkyl chain and DP equal to 1.5); 8.18 wt % octanol as an alcohol functioning as a co-solvent; 12.86 wt % propylene glycol as a freezing point depression agent; and 5.18 wt % demulsifier. The demulsifier was polyoxyethylene (50) sorbitol hexaoleate.

Table 5 shows the turbidity measurements of 2 gpt dilutions of Microemulsions I and J in different brines (2% KCl, 12% API brine, 24% API brine and Bakken C water). Microemulsion I, which incorporates APG surfactant and amyl alcohol, demonstrated robust dilution throughout salinities ranging from about 20,000 ppm TDS to about 310,000 ppm TDS, maintaining a turbidity of less than 15 NTU at all salinities in this range. Meanwhile, Microemulsion J, which incorporated octanol rather than amyl alcohol as the co-solvent, exhibited turbidity in the opaque range demonstrating the instability of Microemulsion J at different salinities, and showing a less robust dilution than Microemulsion I. The difference in dilution between Microemulsion I and Microemulsion J demonstrates the criticality of using certain alcohols as co-solvents as compared to other alcohols. Microemulsions using butanol also show desirable dilution as a co-solvent as demonstrated by Microemulsion A, referenced in Examples 2 and 4.

TABLE 5

| | 2% KCl | 12% API brine | 24% API brine | Bakken C water |
|---|---|---|---|---|
| Microemulsion I | 4.61 NTU | 2.62 NTU | 11.80 NTU | 1.81 NTU |
| Microemulsion J | 29.8 NTU | <200 NTU | <200 NTU | <200 NTU |

Example 8

The turbidity of 2 gpt of Microemulsions K and L were measured through a procedure similar to that described in Example 6.

Microemulsion K used in this example was prepared using 36.0 wt % water; 16.32 wt % methyl ester as solvent; 22.7 wt % APG surfactant ($C_{8-16}$ alkyl chain and DP equal to 1.5); 6.7 wt % amyl alcohol functioning as a co-solvent; 13 wt. % propylene glycol as a freezing point depression agent and 5.25 wt % demulsifier. The demulsifier was polyoxyethylene (50) sorbitol hexaoleate.

Microemulsion L used in this example was prepared using 36.0 wt % water; 16.32 wt % butyl 3-hydroxybutanoate as solvent; 22.7 wt % APG surfactant ($C_{8-16}$ alkyl chain and DP equal to 1.5); 6.7 wt % amyl alcohol functioning as a co-solvent; 13 wt. % propylene glycol as a freezing point depression agent and 5.25 wt % demulsifier. The demulsifier was polyoxyethylene (50) sorbitol hexaoleate.

Table 6 shows the turbidity measurements of 2 gpt dilutions of Microemulsions K and L in different brines (2% KCl, 12% API brine, 24% API brine and Bakken C water). The turbidity results show that Microemlulsions K and L dilute clear in an unexpectedly wide range of salinities. This example also shows that solvents such as butyl 3-hydroxybutanoate and demulsifiers such as polyoxyethylene (50) sorbitol hexaoleate may be used in combination with the APG surfactant microemulsions of the present invention.

TABLE 6

|  | 2% KCl | 12% API brine | 24% API brine | Bakken C water |
|---|---|---|---|---|
| Microemulsion K | 3.50 NTU | 1.94 NTU | 2.44 NTU | 2.83 NTU |
| Microemulsion L | 4.98 NTU | 0.593 NTU | 0.734 NTU | 0.948 NTU |

Example 9

Two samples of Microemulsion A, (Microemulsion A formulation is described in Example 2 above, and incorporated herein by reference) were prepared at 2 gpt in 24% API brine. One sample was kept at 75° F. and the other one was placed for few hours in an oven at 200° F. Each of the samples remained clear (had a turbidity of 15 NTU or less) and did not exhibit phase separation showing the higher tolerance of Microemulsion A comprising APG surfactant within this range of temperatures.

Example 10

Experiments were performed to determine the critical point: the maximum amount of solvent that can be included in the microemulsion while maintaining a clear dilution in brine. Where solvent is present in an amount greater than the critical point, dilution into aqueous brine ceases to be clear. The examples were conducted using 2% KCl as the aqueous brine.

The critical point was determined for microemulsions containing relatively low amounts of APG surfactant and amyl alcohol. Microemulsion M was prepared using 11.605 wt % APG surfactant ($C_{8-16}$ alkyl chain and DP equal to 1.5), 3.94 wt % amyl alcohol, 5.5 wt % demulsifier, 14.10 wt % propylene glycol, the balance being aqueous phase and solvent. The critical point for a 50:50 blend of d-limonene: methyl ester solvent was determined to be 11.33 wt %. Greater amounts of the solvent blend gave dilutions in 2% KCl that were slightly hazy or worse.

The critical point was determined for a microemulsion formulation in which higher amounts of APG surfactant and amyl alcohol were present. Microemulsion N was prepared using 22.27 wt % APG surfactant, 8.2 wt % amyl alcohol, 5.37 wt % demulsifier, 12.78 wt % propylene glycol, the balance being aqueous phase and solvent. The critical point for a 50:50 blend of d-limonene:methyl ester solvent was determined to be 20.34 wt %. Greater amounts of the solvent blend gave dilutions in 2% KCl that were slightly hazy or worse.

The methyl ester used in Example 10 was a $C_{10}$ to a $C_{16}$ aliphatic carboxylic acid ester with one degree of unsaturation in the aliphatic group and the demulsifier was polyoxyethylene (50) sorbitol hexaoleate.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e. elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e. the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element or a list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e. to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A composition for use in an oil and/or gas well having a wellbore, comprising a microemulsion, wherein the microemulsion comprises:
    an aqueous phase;
    a surfactant comprising alkyl polyglycoside;
    a solvent comprising a terpene and a linear oleaginous hydrocarbon solvent; and
    an alcohol having from 1 to 8 carbon atoms, wherein the alcohol comprises butyl 3-hydroxybutanoate.

2. The composition of claim 1, wherein the alcohol further comprises butanol, pentanol, amyl alcohol, or combinations thereof.

3. The composition of claim 1, wherein the alcohol further comprises amyl alcohol.

4. The composition of claim 1, wherein the terpene comprises dipentene or d-limonene.

5. The composition of claim 1, wherein the terpene comprises dipentene and d-limonene.

6. The composition of claim 1, wherein the terpene comprises dipentene.

7. The composition of claim 1, wherein the terpene comprises d-limonene.

8. The composition of claim 1, wherein the alcohol is present in an amount between about 2 wt % and about 15 wt % versus the microemulsion.

9. The composition of claim 8, wherein the terpene comprises dipentene and d-limonene.

10. The composition of claim 1, wherein the microemulsion further comprises an additional alcohol having 1 to 8 carbon atoms.

11. The composition of claim 1, wherein the solvent further comprises a terpene alcohol.

12. The composition of claim 11, wherein the terpene alcohol comprises alpha-terpineol.

13. The composition of claim 1, wherein the microemulsion further comprises a glycol.

14. The composition of claim 1, wherein the solvent further comprises linalool, geraniol, nopol, alpha-terpineol, menthol, eucalyptol, or combinations thereof.

15. The composition of claim 1, wherein the solvent further comprises an alcohol, an aldehyde, an ether, or a ketone group.

* * * * *